Jan. 22, 1974 L. R. STOHL Plant Pat. 3,448
GRAPEVINE
Filed Jan. 6, 1972
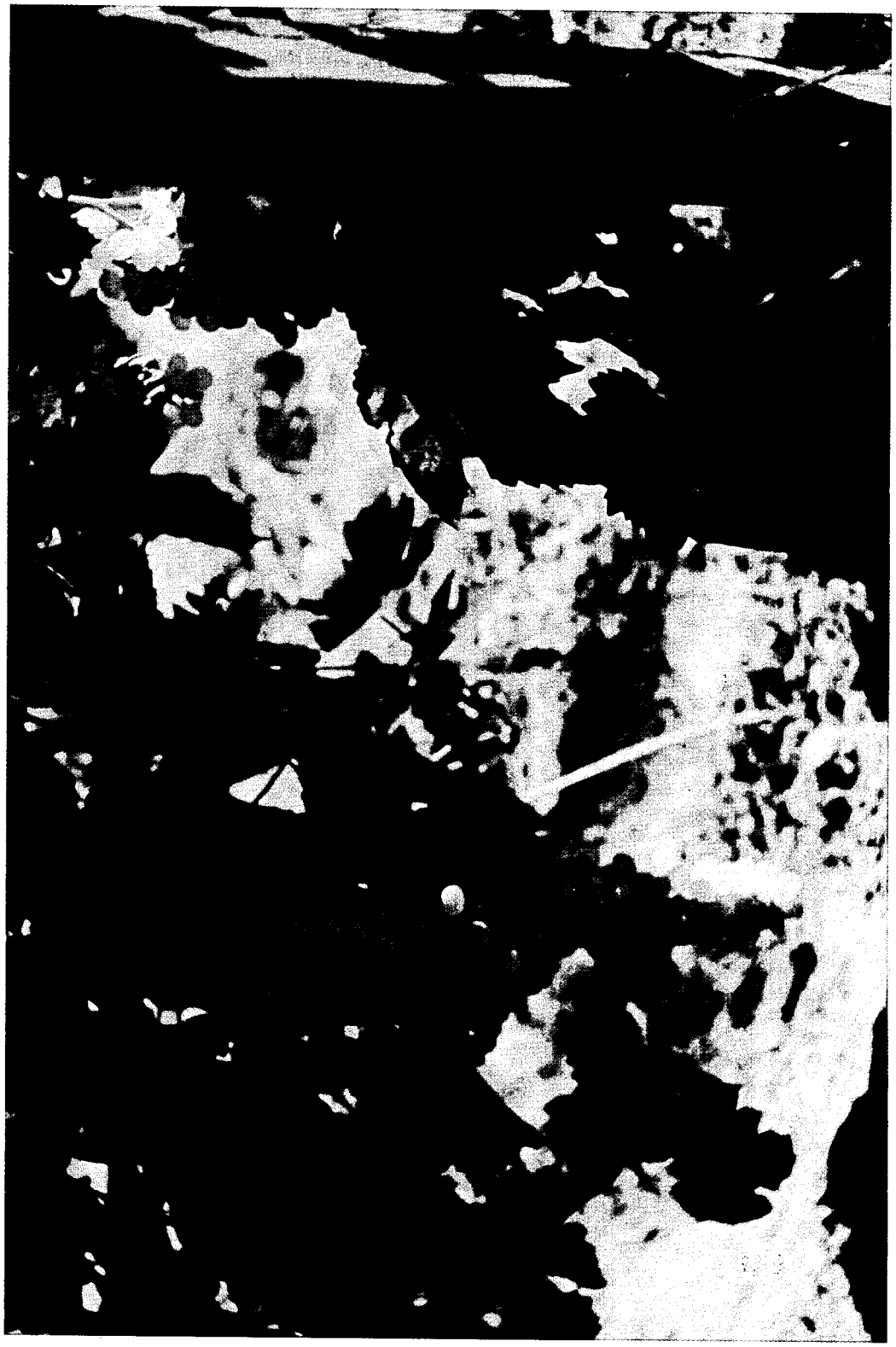

United States Patent Office

Plant Pat. 3,448
Patented Jan. 22, 1974

3,448

GRAPEVINE

Luther R. Stohl, 5895 Avenue 426,
Reedley, Calif. 93654

Filed Jan. 6, 1972, Ser. No. 215,922
Int. Cl. A01h 5/03
U.S. Cl. Plt.—47 1 Claim

ABSTRACT OF THE DISCLOSURE

A new and distinct variety of grapevine characterized principally by its leaves of an orbicular cordate configuration having five clefts dividing five lobes, large seedless berries having less rudimentary embryo and firmer pulp than the berries of the Thompson seedless grape which it most nearly resembles, but from which it is distinguished, growing in large loose clusters less compact and more elongated than the clusters of the Thompson seedless grape and supported by peduncles of a length of from 2 to 4 inches.

The new variety of grapevine was discovered as a chance variation in a vineyard of Thompson seedless (unpatented) grapevines, maintained by the applicant of 5895 Avenue 426, Reedley, Calif. 93654. The climatic conditions existing in the vineyard in which the new variety of grapevine was discovered is comparable to those enjoyed by the San Joaquin Valley and include a mild winter of light rainfall and a hot dry summer.

When discovered, it was noted that the new variety of grapevine bore fruit resembling the berries of the Thompson seedless grape, however, the clusters of the new variety are substantially longer than the Thompson, are loose, and are supported by a substantially longer stem or peduncle. Upon examining the fruit it was noted that the berries tend to be somewhat firmer than those of the Thompson grape and include fewer and smaller rudimentary embryo. Furthermore, the foliage is dense and the leaves include five globes separated by five deep clefts.

After having discovered the new variety, it was observed during several growing seasons and thereafter asexually reproduced by cuttings taken from the parent plant which grew well and exhibited vigorous and healthy qualities of growth. The fruit borne by the vines grown from the cuttings has the distinctive characteristics observed in the fruit of the originally discovered chance variation.

The accompanying drawing, which is an enlarged, mounted color photograph, shows the new variety prior to harvest.

The following is a detailed description of the pomological characteristics of the new variety. Color terminology is in accordance with that of the "Nickerson Color Fan" and dimensions, sizes, colors and other characteristics given are understood to be approximation of averages set forth as accurately as practicable.

Vine:

*Size.*—Large—similar to Thompson.
*Growth.*—Vigorous, drooping and dense.
*Bark.*—Loose and rough.
*Canes.*—Medium in number, of medium thickness, uniform and of medium hardness.
*Tendrils.*—Forked and of medium thickness.
*Color.*—Brilliant yellow green (5 G Y 8/8).

Leaves:

*Number.*—Average—similar to Thompson.
*Size.*—Width—six inches, length—seven inches.

*Shape.*—Generally obicular cordate, having five lobes divided by five deep clefts.
*Color.*—Moderately Yellow Green (7.5 G Y 5/7) in color with the upper surface being lighter in color than the lower surface.
*Margin.*—Crenate.
*Teeth.*—Medium wide, short and rounded.
*Midrib.*—Four to five inches, straight and light.
*Petiolar Sinus.*—Medium deep, narrow and open.
*Lateral Sinus.*—Four in number, deep, narrow and open.
*Petiole.*—Two to four inches in length. Medium, smooth, glabrous, enlarged at base.

Fruit:

*Maturity.*—Similar to Thompson—early August.
*Production.*—Heavy.
*Cluster.*—Five to six inches in width, sixteen to eighteen inches in length, conical in shape, double shouldered, one to two per shoot and medium loose.
*Secondary Branches.*—Medium long.
*Peduncle.*—Length—two to four inches long and a medium thickness.
*Pedicle.*—Length—one-fourth of an inch, medium slender, and adheres to the stem.
*Brush.*—Short, slender, stringy and adheres to pedicel.
*Berry.*—Three-quarters of an inch in length and one-half inch in diameter and uniformly cylindrical.
*Skin.*—Medium tough, medium thick, and adheres to the pulp.
*Dots.*—Not prominent.
*Pulp.*—Medium crisp, medium dry and sweet.
*Juice.*—No color.
*Saccharine.*—Normal.
*Flavor.*—Neutral.
*Uses.*—Fresh table, raisins and wine.
*Embryo.*—Less rudimentary embryo than Thompson seedless.
*Special identifying characteristics.*—Different leaf-type, more elongated clusters, firmer berries and longer peduncle than the Thompson seedless which it most nearly resembles but distinguishes therefrom.

The new variety grapevine has been described as it exists under the ecological conditions prevailing in the central San Joaquin Valley of California. Normal variations can be expected under different environmental conditions.

Having thus described the instant grapevine, I claim:

1. A new and distinct variety of grapevine substantially as illustrated and described, characterized principally by its leaves of an orbicular cordate configuration having five clefts dividing five lobes, large seedless berries having less rudimentary embryo and firmer pulp than the berries of the Thompson seedless grape which it most nearly resembles, but from which it is distinguished, growing in large loose clusters less compact and more elongated than the clusters of the Thompson seedless grape and supported by peduncles of a length of from 2 to 4 inches.

No references cited.

ROBERT E. BAGWILL, Primary Examiner